US006518244B2

United States Patent
Cardin et al.

(10) Patent No.: US 6,518,244 B2
(45) Date of Patent: Feb. 11, 2003

(54) COMBINATIONS OF HEPARIN COFACTOR II AGONIST AND PLATELET IIB/IIIA ANTAGONIST, AND USES THEREOF

(75) Inventors: Alan D. Cardin, Cincinnati, OH (US); Cornelius L. Van Gorp, Springboro, OH (US)

(73) Assignee: IntimaX Corporation, Cincinnati, OH (US)

(*) Notice: Subject to any disclaimer, the term of this patent is extended or adjusted under 35 U.S.C. 154(b) by 57 days.

(21) Appl. No.: 09/802,775

(22) Filed: Mar. 9, 2001

(65) Prior Publication Data

US 2001/0036932 A1 Nov. 1, 2001

Related U.S. Application Data

(60) Provisional application No. 60/188,085, filed on Mar. 9, 2000.

(51) Int. Cl.$^7$ .................. A61K 38/12; A61K 31/715
(52) U.S. Cl. ............................. 514/11; 514/54
(58) Field of Search ...................... 514/11, 54

(56) References Cited

U.S. PATENT DOCUMENTS

| | | | |
|---|---|---|---|
| 5,013,724 A | 5/1991 | Petitou et al. | 514/54 |
| 5,227,490 A | 7/1993 | Hartman et al. | 514/317 |
| 5,281,585 A | 1/1994 | Duggan et al. | 514/79 |
| 5,294,616 A | 3/1994 | Duggan et al. | 514/255 |
| 5,312,923 A | 5/1994 | Chung et al. | 546/185 |
| 5,470,849 A | 11/1995 | Callahan et al. | 514/212 |
| 5,547,944 A | 8/1996 | Mascellani et al. | 514/54 |
| 5,635,477 A * | 6/1997 | Degrado et al. | 514/11 |
| 5,731,324 A | 3/1998 | Fisher et al. | 514/320 |
| 5,922,690 A * | 7/1999 | Van Gorp et al. | 514/54 |
| 5,952,306 A | 9/1999 | Hartman et al. | 514/18 |
| 5,968,902 A | 10/1999 | Scarborough et al. | 514/9 |
| 5,972,967 A | 10/1999 | Gelotte | 514/331 |
| 5,976,532 A | 11/1999 | Coller et al. | 424/133.1 |
| 5,993,797 A | 11/1999 | Kitazato et al. | 424/78.3 |
| 6,001,961 A | 12/1999 | Jonczyk et al. | 530/317 |
| 6,008,193 A | 12/1999 | Garfinkel et al. | 514/12 |
| 6,013,625 A | 1/2000 | Pierschbacher et al. | 514/9 |
| 6,022,523 A | 2/2000 | DeGrado et al. | 424/1.69 |

FOREIGN PATENT DOCUMENTS

| | | |
|---|---|---|
| CA | 2000650 | 10/1989 |
| DE | 3124384 | 1/1983 |
| EP | 554898 | 8/1993 |
| EP | 668875 | 8/1995 |
| FR | 2584728 | 1/1987 |
| WO | WO 93/05075 | 3/1993 |
| WO | 94/09034 | 4/1994 |
| WO | WO 97/35592 | 10/1997 |
| WO | WO 99/38827 | 8/1999 |

OTHER PUBLICATIONS

Nicolini et al. Chem. Abst. 121:170,096 (1994).*
Pavao et al, "A Unique Dermatan Sulfate–Like Glycosaminoglycan from Ascidian," *J. Biol. Chem.*, (Dec. 29, 1995) 270(52):31027–31036.
Poupard et al, "Antibodies to Platelet Factor 4–Heparin After Cardiopulmonary Bypass in Patients Anticoagulated with Unfractionated Heparin or a Low Molecular Weight Heparin:clinical Implications for Heparin–Induced Thrombocytopenia," *Circulation* (1999) 99:2539–2536.
Prandoni et al, "Dermatan Sulfate: a Safe Approach to Prevention of Postoperative Deep Vein Thrombosis," *Br. J. Surg.* (1992) 79(6):505–509.
Adgey, "Bleeding Complications with New Antithrombotics Used in Ischemic Heart Disease," *Haemostasis* (1996) 26(5):237–246.
Agnelli et al, "A Randomized Double–Blind, Placebo–Controlled Trial of Dermatan Sulphate for Prevention of Deep Vein Thrombosis in Hip Fracture," *Thromb. Haemostas.* (1992) 67:203–208.
Agnelli, "New Antithrombins and Nonheparin Glycosaminoglycans in Clinical Development," *Vessels* (1995) 1:9–16.
Ali et al, "Diffuse Alveolar Hemorrhage Following Administration of Tirofiban or Abciximab: a Nemesis of Platelet Glycoprotein IIb/IIIa Inhibitors," *Catheter Cardiovasc. Interv.* (2000) 49(2):181–184.
Andreozzi et al, "Tolerability and Clinical Efficacy of Desmin in the Treatment of Superficial Thrombovaricophlebitis," *Angiology* (1996) 47(9):887–894.
Barbanti et al, "Therapeutic Effect of a Low Molecular Weight Dermatan Dulphate (Desmin 370) in Rat Venous Thrombosis–Evidence for an Anticoagulant–Independent Mechanism," *Thromb. Haemost.* (1993) 69(2):147–151.
Bauer et al, "Prevalence of Heparin–Associated Antibodies without Thrombosis in Patients Undergoing Cardiopulmonary–Bypass Surgery," *Circulation* (1997) 95:1242–1246.
Bendayan et al, "Dermatan Sulfate Is a More Potent Inhibitor of Clot–Bound Thrombin than Unfractionated and Low Molecular Weight Heparins," *Thromb. Haemost.* (1994) 71(5):576–580.
Bergonzini et al, "Pharmacokineics of Native and Low Molecular Weight Dermatans: Preliminary Studies in Rats and Primates," *Seminars in Thrombosis and Hemostasis, Sup 2* (1990):235–239.

(List continued on next page.)

Primary Examiner—Peter O'Sullivan
(74) *Attorney, Agent, or Firm*—Hasse Guttag & Nesbitt LLC; Eric W. Guttag

(57) ABSTRACT

Combined use of a heparin cofactor II agonist and a platelet GPIIb/IIIa receptor antagonist to inhibit both platelet aggregation and thrombin generation resulting from disease, injury or responses to wound repairs. The combined use of the heparin cofactor II agonist and the platelet GPIIb/IIIa receptor antagonist can achieve these therapeutic benefits while at the same time minimizing or reducing the risk of hemorrhagic side effects (e.g., prolonged bleeding), and without causing undesired antigenic responses. Moreover, certain subtherapeutic amounts of the heparin cofactor II agonist with certain subtherapeutic amounts of a platelet GPIIb/IIIa receptor antagonist can, in combination, be therapeutically effective in inhibiting both platelet aggregation and thrombin generation.

20 Claims, No Drawings

OTHER PUBLICATIONS

Blankenship, "Bleeding Complications of Glycoprotein IIb–IIIa Receptor Inhibitors," *Am. Heart J.* (1999) 138(4 pt. 2):287–296.

Bode et al, "Antithrombotic Potency of Hirudin Is Increased in Nonhuman Primates by Fibrin Targeting," *Circulation* (1997) 95(4):800–804.

Bode et al, "Fibrin–Targeted Recombinant Hirudin Inhibits Fibrin Deposition on Experimental Clots More Efficiently than Recombinant Hirudin," *Circulation*(1994) 90(4):1956–1963.

Bara et al, "Platelet Factor 4 Inhibits Unfractionated Heaparin, LMWH, But Does Not Inhibit Drugs With Exclusive Direct Anti Xa or Anit IIa Activity," p. 576.

Brister et al, "Effect of Heparin and CL–0313 on Complement Activation In Vitro and Thrombin Generation During Cardiopulmonary Bypass In Vivo," *Haemostasis* (1996) 26: 575.

Brister et al, "Heparinless Cardiopulmonary Bypass Revisited: a Newer Strategy to Avoid Heparin–Related Bleeding Using Dermatan Sulfate," *J. Cardiothorac. Anesth.* (1995) 9(3):317–321.

Brister et al, "Is Heparin the Ideal Anticoagulant for Cardiopulmonary Bypass? Dermatan Sulphate May be an Alternate Choice," *Thromb. Haemostas.*, (1999) 71:468–473.

Bratt et al, "A Comparison Between Low Molecular Weight Heparin (KABI 2165) and Standard Heparin in the Intravenous Treatment of deep Venous Thrombis," *Thromb. Haemostas.*, (1985) 54(4):813–817.

Gammie et al, "Abciximab and Excessive Bleeding in Patients Undergoing Emergency Cardiac Operations," Ann. Thorac. Surg. (1998) 65(2):465–469.

Buchanan et al, "A Rationale for Targeting Antithrombotic Therapy at the Vessel Wall: Improved Antithrombotic Effect and Decreased Risk of Bleeding," *Wien Klin Wochenschr* (1999) 111: 81–89.

Buchanan et al, "Inhibition of Chronic Vessel Wall Intimal Hyperplasia Following Acute Anticoagulant Treatment: Relative Effects of Heparin and Dermatan Sulphate," *Thrombosis Res.* (1998) 91:157–167.

Cadroy et al "Dermatan Sulfate Inhibition of Fibrin–Rich Thrombus Formation in Nonhuman Primates," *Arterioscler. Thromb.* (1993) 13(8):1213–1217.

Ciacca et al, "Arginine 200 of Heparin Cofactor II Promotes Intramolecular Interactions of the Acidic Domain: Implications for Thrombin Inhibition," *J. Biol. Chem.* (1997) 272(22):14074–14079.

Cohen et al, "A Dose Ranging Study to Evaluate Dermatan Sulphate in Preventing Deep Vein Thrombosis Following Total Hip Arthroplasty," *Thromb. Haemostas.* (1994) 72(6):793–798.

Confrancesco et al, "Dermatan Sulphate for the Treatment of Disseminated Intravascular Coagulation (DIC) in Acute Leukemia: a Randomised, Heparin–Controlled Pilot Study," *Thromb. Res.* (1994) 74(1):65–75.

Dangas et al, "Effects of Platelet Glycoprotein IIb/IIIa Inhibition with Abciximab on Thrombin Generation and Activity during Percutaneous Coronary Intervention," *Am. Heart J.* (1999) 138(1 Pt.1):49–54.

Di Carlo et al, "Dermatan Sulphate for the Prevention of Postoperative Venous Thromboembolism in Patients with Cancer: DOS (Dermatan Sulphate in Oncology Survey) Study Group," *Thromb. Haemost.* (1999) 82(1):30–34.

Dunstone et al, "Ion–Exchange Reactions Between Acid Mucopolysaccharides and Various Cations," *Biochem.J.* (1962) 85(3):336–351.

Eisenberg et al, "Platelet–Dependent and Procoagulant Mechanisms in Arterial Thrombosis," *Int. J. Cardiol.* (1999) 68(suppl.1):S3–S10.

Fareed et al, "Molecular and Functional Heterogeneity in Dermatan Sulfate Preparations," *Seminars in Thrombosis and Hemostasis* (1991) 17(supp 2):174–180.

Fehr et al, "In Vivo Complement Activation by Polyanion–Polycation Complexes: Evidence that C5a Is Generated Intravascularly During Heparin–Protamine Interaction," *Clin. Immunol. Immunopathol.* (1983) 29(1):7–14.

Fenton et al, "Thrombin and Antithrombotics," *Semin. Thromb. Hemostas.* (1998) 24: 87–91.

Fernandez et al, "Catalysis of Thrombin Inhibition Provides an Index for Estimating the Antithrombotic Potential of Glycosaminoglycans in Rabbits," *Thromb. Haemostas.* (1987):286–293.

Fernandez et al, "The Haemorrhagic and Antithrombotic Effects of Dermatan Sulphate," *Br. J. Haematol.* (1986) 64:309–317.

Ferrari et al, "Preliminary Chemical, Biochemical, and Pharmacological Characterization of a Low Molecular Weight Dermatan Sulphate," *Carbohydrate Res.* (1994)255(3):125–132.

Francis et al, "Thrombin Activity of Fibrin Thrombi and Soluble Plasmic Derivatives," *J. Lab. Clin. Med.* (1983) 102:220–230.

Fredenburgh et al, "Evidence for Allosteric Linkage Between Exosites 1 and 2 of Thrombin," *J. Biol. Chem.* (1997) 272(41):25493–25499.

Furie et al., "Molecular and Cellular Biology of Blood Coagulation," *N. Eng. J. Med.* (1992) 326: 800–806.

Furman et al, "The Cleaved Peptide of the Thrombin Receptor Is a Strong Platelet Agonist," *Proc. Natl. Acad. Sci.* (1998) 95(6):3082–3087.

Gianese et al, "The Pharmacokinetics and Pharmacodynamics of Dermatan Sulfate MF7701 During Haemodialysis for Chronic Renal Failure," *Brit J. Clin. Pharm.* (1993) 35:335–339.

Gillum et al, "Coronary Revascularization and Cardiac Catheterization in the United States: Trends in Racial Differences," *JACC* (1977) 29(7):1557–1562.

GISSI–2, "A Factorial Randomized Trial of Alteplase Versus Streptokinase and Heparin Versus No Heparin Among 12,490 Patients with Acute Myocardial Infarction," *Lancet* (1990) 1:65–71.

Gorman et al, "Cardiopulmonary Bypass, Myocardial Management, and Support Techniques," *J. Thoracic Card. Surgery* (1996) 111(1):1–12.

Haralabopoulos et al, "Thrombin Promotes Endothelial Cell Alignment in Matrigel In Vitro and Angiogenesis In Vivo," *Am. J. Physiol.* (1997):C239–245.

Hogg et al, "Fibrin Monomer Protects Thrombin from Inactivation by Heparin–Antithrombin III: Implications for Heparin Efficacy," *Proc. Natl. Acad. Sci. U.S.A.* (1989) 86:3619–23.

Hoppensteadt et al, "Effect of Dermatan Sulfate and Heparin Sulfate on Platelet Activity Compared to Heparin," *Semin. Thromb. Hemost.* (1991) 17(suppl 1):60–64.

Hortin et al, "Antithrombin Activity of a Peptide Corresponding to Residues 54–75 of Heparin Cofactor II," *J. Biol. Chem.* (1989) 264(24):13979–13982.

Hortin et al, "Identification of Two Sites of Sulfation of Human heparin Cofactor II," *J. Biol. Chem.* (1986) 261:15827.

Hsieh, "Thrombin Interaction with Fibrin Polymerizing Sites," *Thromb. Res.* (1997) 86: 301–316.

Jubelirer et al, "Acute Profound Thrombocytopenia Following C7E3 Fab (Abciximab) Therapy: Case Reports, Review of the Literature and implications for Therapy," *Am.J. Hematol.* (1999) 61(3):205–208.

Kasirer–Friede et al., "Thrombin Receptor Occupancy Modulates Aggregation Efficiency and Platelet Surface Expression of vWF and Thrombospondin at Low Thrombin Concentrations" (1999) *Thromb. Haemost. 81*: 967–975.

Klement et al, "Hirudin Causes More Bleeding than Heparin in a Rabbit Ear Bleeding Model," *J. Lab. Clin. Med.* (1998) 132(3):181–185.

Krupinski et al, "Dermatan Sulfate Enhances the Lysis of Laser–Induced Thrombus In Vivo," *Thromb. Res.* (1998) 91:199–202.

Kumar et al, "The Influence of Fibrinogen and Fibrin on Thrombin Generation–Evidence for Feedback Activation of the Clotting System by Clot Bound Thrombin," *Thromb. Hemost.* (1994) 72: 713–721.

Liaw et al, "Comparison of Heparin–and Dermatan Sulfate–Mediated Catalysis of Thrombin Inactivation by Heparin Cofactor II," *J. Biol. Chem.* (1999) 274(39):27597–27604.

Linhardt et al, "Low Molecular Weight Dermatan Sulfate as an Antithrombotic Agent: Structure–Activity Relationship Studies," *Biochem. Pharmacol.* (1994) 47(7):1241–1252.

Linhardt et al, "Dermatan Sulfate as Potential Therapeutic Agent," *Gen. Pharmar.* (1995), 26(3):443–451.

Linhardt et al, "Structural Features of Dermatan Sulfates and Their Relationship to Anticoagulant and Antithrombotic Activities," *Biochem. Pham.* (1991) 42(8):1609–1619.

Liu et al, "The Binding of Thrombin to Fibrin," *J. Biol. Chem.* (1979) 254: 10421–10425.

Maaroufi et al, "Influence of the Oversulfation Method and the Degree of Sulfation on the Anticoagulant Properties of Dermatan Sulfate Derivatives," *Thromb. Res.* (1990) 59:749–758.

Lyle et al, "Assessment of Thrombin Inhibitor Efficacy in a Novel Rabbit Model of Simultaneous Arterial and Venous Thrombosis," *Thromb. Haemost.* (1998) 79(3):656–662.

Mascellani et al, "Active Site for Heparin Cofactor II in Law Molecular Mass Dermatan Sulfate: Contribution to the Antithrombotic Activity of Fractions with High Affinity for Heparin Cofactor II," *Thromb. Res.* (1996) 84(1):21–32.

Mascellani et al, "Quantitation of Dermatan Sulfate Active Site for Heparin Cofactor II by $^1$H Nuclear Magnetic Resonance Spectroscopy," *Anal. Biochem.* (1994)223:135–141.

Mascellani et al, "Relative Influence of Different Disulphate Disaccharide Clusters on the HCII–Mediated Inhibition of Thrombin by Dermatan Sulfates of Different Origins," *Thromb. Res.* (1994) 74:605–615.

Matthiasson et al, "Prevention of Experimental Venous Thrombosis in Rabbits with Different Low Molecular Weight Heparins, Dermatan Sulphate and Hirudin," *Haemostasis* (1995) 25(3):124–132.

Matthiasson et al, "The Haemorrhagic Effect of Low Molecular Weight Heparins, Dermatan Sulphate and Hirudin," *Haemostasis* (1995) 25:203–211.

Medynski et al., "Synthetic Peptide Combinatorial Libraries," *Bio/Technology* (1994) 12:709–710.

Maimone et al, "Structure of a Dermatan Sulfate Hexasaccharide that Binds to Heparin Cofactor II with High Affinity," *J. Biol. Chem.* (1990) 265:1863–1871.

Morel et al, "C5a and Thromboxane Generation Associated with Vaso–and Broncho–Constriction During Protamine Reversal of Heparin," *Anesthesiology* (1987) 66(5):597–604.

Mousa et al, "Intranasal Antiplatelet/Antithrombotic Efficacy of a Novel Platelet GPIIB/IIIA Receptor Antagonist DMP755," *Thromb. Res.* (1998) 92:115–124.

Brister et al, "Thrombin Generation during Cardiac Surgery: Is Heparin the Ideal Anticoagulant?," *Thromb. Haemostas.* (1993) 70(2):259–262.

Buchanan et al, "Evidence for a Conformational Change of Surface–Bound Thrombin that Promotes Vessel Wall Thrombogenicity: Selective and Sustained Inhibition of its Activity by Intimatan But not by Heparin," *Thromb. Haemost.* (1999) ISTH(Suppl):413.

Buchanan et al, "Selective and Sustained Inhibition of Surface–Bound Thrombin Activity by Intimatan/Heparain Cofactor ** and its Relevence to Assessing Systemic Anticoagulation in Vivo, Ex Vivo and in Vitro," (Oct. 23, 2000).

Demir et al., "Ecarin Clotting Time is Sensitive to Heparinoids: Comparison of Two different Techniques," *Clin. Appl. Thromb. Hemost.* (2001) 7: 38–43.

Gast et al, "Inhibiton of Clot–Bound and Free (Fluid–Phase Thrombin) by a Novel Synthetic Thrombin Inhibitor (Ro 46–6240), Recombinant Hirudin and Heparin in Human Plasma," *Blood Coagul. Fibrinolysis* (1994) 5(6):879–887.

Hayakawa et al., "Inhibition of Thrombin by Sulfated Polysaccharides Isolated from Green Algae," *Biochim. Biophys. Acta* (2000) 30: 86–9.

Huhle et al, "Immunologic Response to Recombinant hirudin in HIT Type II Patients during Long–Term Treatment," *Br. J. Haematol.* (1999) 106(1):195–201 (appendix U).

Kleiman et al, "Inhibition of Platelet Aggregation with a Glycoprotein IIb–IIIa Antagonist Does Not Prevent Thrombin Generation in Patients Undergoing Thrombolysis for Acute Myocardial Infarction," *J. Thromb. Thrombolysis* (2000) 9(1):5–12.

Liaw et al, (Molecular Basis for the Susceptibility of Fibrin–Bound Thrombin to Inactivation by Heparin Cofactor II in the Presence of Dermatan Sulfate but Not Heparin, *J. Biol. Chem.* (2001) 276(24): 20956–20965.

O'Neil et al., Identification of Novel Peptide Antagonists for GPIIb/IIIa from a Conformationally Constrained Phage Peptide Library, *Proteins: Struct Func Genet* (1992) 14:509–515.

Thomas et al, "Relative Efficacy of Heparin and Related Glycosaminoglycans as Antithrombotic Drugs," *Ann. N.Y. Acad. Sci.*, (1989) 556:313–322.

Zucker et al, "Platelet Activation," *Arteriosclerosis* (1985) 5(1):2–18.

Murata et al, "Occurrence of an Oversulfated Dermatan Sulfate in Kidney Tissue," *Renal Physiol.* (1978) 1(1);48–55.

Myles et al, "Role of Thrombin Anion–Binding Exosite–I in the Formation of Thrombin–Serpin Complexes," *J. Biol. Chem.* (1998) 273(47):31203–31208.

Nagasawa et al, "Chemical Sulfation of Preparations of Chrondoitin 4– and 6–Sulfate, and Dermatan Sulfate Preparation of Chondroitin Sulfate E–Like Materials From Chondroitin 4–Sulfate," *Carbohydrate Research*, 158, No. 1 (Dec. 1986), pp. 183–190, Amsterdam, Netherlands.

Nurmohamed et al, "Clinical Experience with a New Antithrombotic (Dermatan Sulfate) in Chronic Hemodialysis Patients," Clin. Neph., (1993) 39:166–171.

Ofosu et al, "Heparan Sulfate and Dermatan Sulfate Inhibit the Generation of Thrombin Activity in Plasma by Complementary Pathways," Blood, (1984) 64(3):742–747.

Ofosu et al, "Increased Sulphation Improves the Anticoagulant Activities of Heparan Sulphate and Dermatan Sulphate," Biochem. J., (1987) 248:889–896.

Ofosu et al, "Plasma Anticoagulant Mechanisms of Heparin, Heparin Sulfate, and Dermatan Sulfate," Ann. NY Acad. Sci. (1989) 556:123–131.

Ofosu et al, "Thrombin–Catalyzed Amplification and Inhibitory Reactions of Blood Coagulation," CRC Press (1995) pp. 1–18.

Okwusidi et al, "Fibrin Moderates the Catalytic Action of Heparin But Not that of Dermatan Sulfate on Thrombin Inhibition in Human Plasma," J. Lab. Clin. Med. (1991) 117:359–364.

Okwusidi et al, "In Vivo Catalysis of Thrombin Inhibition by Antithrombin III or Heparin Cofactor II and Antithrombotic Effect: Differential Effects of Unfractionated Heparin and Dermatan Sulphate," Thromb. Haemorrh. Disorders (1990) 1:77–80.

Onaya et al, "Effects of Dermatan Sulfate, a Heparin Cofactor II Mediated Thrombin Inhibitor, on the Endotoxin–Induced Disseminated Intravascular Coagulation Model in the Rat: Comparison with Low–Molecular Weight Heparin, Nafamostat Mesilate and Argathroban," Jpn. J. Pharmacol. (1998) 76(4):397–404.

Pratico et al, "Interaction of a Thrombin Inhibitor and a Platelet GPIIb/IIIa Antagonist In Vivo: Evidence that Thrombin Mediates Platelet Aggregation and Subsequent Thromboxane A2 Formation during Coronary Thrombolysis," J. Pharmacol. Exp. Ther. (1997) 281(3):1178–1185.

Rogers et al, "Role of Thrombin Exosites in Inhibition by Heparin Cofactor II," J. Biol. Chem. (1992) 267(6):3613–36–17.

Ryan et al, "Antithrombotic Properties of Dermatan Sulfate (MF701) in Haemodialysis for Chronic Renal Failure," Thromb. Haemostas., (1992) 68:563–569.

Santro et al,"Pharmacologic Profile of a Native Dermatan Sulfate," Thromb. Res. (1992) 67(2):201–211.

Sheehan et al, "Heparin Cofactor II Is Regulated Allosterically and Not Primarily by Template Effects: Studies with Mutant Thrombins and Glycosaminoglycans," J. Biol. Chem. (1994) 269(52):32745–32751.

Sheehan et al, "Mutagenesis Selectively Modulates Inhibition by Serpins Heparin Cofactor II and Antithrombin III: Interaction with the Anion–Binding Exosite Determines Heparin Cofactor II Specificity," J. Biol. Chem. (1993) 268(5):3638–3645.

Sheu et al, "Interaction of Thrombin–Activated Platelets with Extracellular Matrices (Fibronectin and Vitronectin): Comparison of the Activity of Arg–Gly–Asp–Containing Venom Peptides and Monoclonal Antibodies Against Glycoprotein IIb/IIIa Complex," J. Pharm. Pharmacol. (1997) 49(1):78–84.

Sitges et al, "Massive Pulmonary Hemorrhage in a Patient Treated with a Platelet Glycoprotein IIb/IIIa Inhibitor," Int. J. Cardiol. (1997) 62(3):269–271; Gammie et al, C.M. Ann. Thorac. Surg. (1998) 65(2):465–469.

Smith at al., "Platelet Responses to Compound Interactions with Thrombin" Biochemistry (1999) 38: 8936–8947.

Song et al, "Generation of Anti–Hirudin Antibodies in Heparin–Induced Thrombocytopenic Patients Treated with r–Hirudin," Circulation (1999) 100(14):1528–1532.

Taliani et al, "Dermatan Sulphate in Patients with Heparin–Induced Thrombocytopenia," Br. J. Haematol. (1999) 104(1):87–89.

Tcheng, "Clinical Challenges of Platelet Glycoprotein IIb/IIIa Receptor Inhibitor Therapy: Bleeding, Reversal, Thrombocytopenia, and Retreatement," Am. Heart J. (2000) 139(2 pt. 2):S38–45.

Tollefsen et al, "Activation of Heparin Cofactor II by Dermatan Sulfate," J. Biol. Chem. (1983) 258(11):6713–6716.

Tollefsen, "The Interaction of Glycosaminoglycans with Heparin Cofactor II: Structure and Activity of a High–Affinity Dermatan Sulfate Hexasaccharide," Heparin and Related Polysaccharides (Ed. Lane D.A., New York 1992:167–176.

Tollefsen et al, "Heparin Cofactor II. Purification and Properties of a Heparin–Dependent Inhibitor of Thrombin in Human Plasma," J. Biol. Chem. (1982) 257:2162–2169.

Trossaert et al, "High Incidence of Anti–Heparin/Platelet Factor 4 Antibodies After Cardiopulmonary Bypass surgery," Br. J. Haematol. (1998) 101(4):653–655.

Vahdat et al, "Fatal Cerebral Hemorrhage and Severe Thrombocytopenia during Abciximab Treatment," Catheter Cardiovasc. Interv. (2000) 49(2):177–180.

Van Deerlin et al, "The N–Terminal Acidic Domain of Heparin Cofactor II Mediates the Inhibition of Alpha–Thrombin in the Presence of Glycosaminoglycans," J. Biol. Chem. (1991) 266(30):20223–20231.

Van Ryn–McKenna, "Dermatan Sulfate: A New Concept in Antithrombotic Therapy," Diss. Abstr. Int., (1993) B 53: 5662.

Volpi et al, "Dermatan Sulfate from Beef Mucosa: Structure, Physicochemical and Biological Properties of Fractions Prepared by Chemical Depolymerization and Anion–Exchange Chromatography," Carbohydrate Res., (1994), 255:133–144.

Volpi et al, "Physico–Chemical Properties and the Structure of Dermatan Sulfate Fractions Purified from Plasma after Oral Administration in Healthy Human Volunteers," Thromb. Haemostas., 75 (1996), pp. 491–496.

Walenga et al, "Clinical Experience with Combined Treatment of Thrombin Inhibitors and GPIIb/IIIa Inhibitors in Patients with HIT," Semin. Thromb. Hemost. (1999) 25(suppl. 1):77–81.

Weitz et al, "Clot–Bound Thrombin Is Protected from Inhibition by Heparin–Antithrombin III but Is Susceptible to Inactivation by Antithrombin III–Independent Inhibitors," J. Clin. Invest. (1990) 86: 385–391.

Whinna et al, "Interaction of Heparin Cofactor II with Biglycan and Decorin," J. Biol. Chem., (1993) 268:3920–3924.

Wallentin, "Effects of Recombinant Hirudin (Epirudin) Compared with Heparin on Death, Myocardial Infarction, Refractory Angina, and Revascularization Procedures in Patients with Acute Myocardial Ischemia without ST Elevation: a Randomized Trial," Organisation to Assess Strategies for Ischemic Syndromes (OASIS–2) Investigators. Lancet (1999) 353:423–424.

Bar–Shavit et al, "Binding of Thrombin to Subendothelial Extracellular Matrix," *J. Clin. Lab Med.* (1991) 117:359–364.

Brandjes et al, "Acenocoumarol and Heparin Compared with Acenocoumarol Alone in the Initial Treatment of Proximal Vein Thrombosis," *Thromb Haemost.* (1985) 54:813–817 (Abstract Only).

Gollnick, "Allergy to Heparin, Heparinoids, and Recombinant Hirudin: Diagnostic and Therapeutic Alternatives," *Hautarzt* (1999) 50(6):406–411 (Abstract Only).

Kwapis et al, "Prolonged Bleeding After Cardiopulmonary Bypass with Recombinant Hirudin," *Eur. J. Cardiothorac. Surg.* (1999) 16(2):256–257 (Abstract Only).

Rao et al, "Glycoprotein IIb/IIIa Receptor Antagonist Tirofiban Inhibits Thrombin Generation during Cardiopulmonary Bypass in Baboons," *Thromb. Haemost.* (1999) 82(1):140–144 (Abstract Only).

Utley, "Cardiopulmonary Bypass Surgery," *Curr Opin. Cardiol.* (1992) 7(2):267–275 (Abstract Only).

Yang et al, "Intimatan, a Heparin Cofactor II Catalyst, Inhibits Vessel Wall Thrombogenicity and Intimal Hyperplasia More Effectively than Heparin," *Thromb. Haemost.* (1999) Suppl.:414.

* cited by examiner

COMBINATIONS OF HEPARIN COFACTOR II AGONIST AND PLATELET IIB/IIIA ANTAGONIST, AND USES THEREOF

CROSS-REFERENCE TO RELATED APPLICATIONS

This application claims the benefit of copending U.S. Provisional Patent Application Serial No. 60/188,085, filed Mar. 9, 2000.

TECHNICAL FIELD

The present application relates to combinations of a heparin cofactor II agonist and a platelet glycoprotein IIb/IIIa receptor (GPIIb/IIIa) antagonist that are useful in inhibiting both platelet aggregation and thrombin generation resulting from disease, or injury responses to wound repairs. The present application particularly relates to the use of subtherapeutic amounts of a heparin cofactor II agonist and subtherapeutic amounts of a platelet GPIIb/IIIa receptor antagonist that, in combination, are therapeutically effective in inhibiting both platelet aggregation and thrombin generation.

BACKGROUND OF THE INVENTION

Cardiovascular disease is the primary cause of death in the USA. According to the American Heart Association, 2.5 million individuals suffer from venous thrombosis and 600,000 suffer from pulmonary embolism each year. In 1996, approximately 830,000 cardiac surgeries and 700,000 cardiac catheterization procedures were performed in the USA as a result of arterial and venous thromboses. Usually, anticoagulant therapy is implemented either alone or in combination with anti-platelet and/or anti-fibrinolytic therapies, particularly in acute care settings where the immediate reopening of a blocked vessel becomes imperative. The drugs used in these therapies, however, have certain dose-limiting side effects, the foremost being hemorrhagic (i.e., prolonged bleeding) and when used in combination, these side effects can become potentiated, further limiting effective dosing and duration of the needed drug treatment. See Fareed, "Drug Interactions with Antiplatelet Agents" *IBC 3$^{rd}$ Annual Mini-Symposium on Advances in Antiplatelet Therapies* (Waltham, Mass. 2000).

With current anticoagulants, the bleeding effects are due to an action on one or more of the enzymes that regulate hemostasis in the global circulation, versus their action in a more specific and limited sense on enzymes of the hemostatic mechanism that promote the disease process at the vascular wall, e.g., low selectivity. Likewise, antiplatelet drugs exhibit strong interactions with the anticoagulants (such as heparin), antithrombin drugs and thrombolytic agents, and safety considerations, for example, preclude their administration to patients at high risk for intracranial hemorrhage, particularly elderly patients with poorly controlled hypertension and previous manifestations of cerebrovascular disease.

Central to this problem is control of thrombin generation and activity. This enzyme plays a key role in the formation of venous and arterial occlusions and in the causation of platelet emboli. Also key to this problem is achieving the sustained inhibition of thrombin at the diseased site which otherwise perpetuates its continued generation in an unabated fashion through a thrombin feedback mechanism that drives clot growth and platelet activation. A more targeted inhibition of thrombin at the disease site and the platelet surface using agents or drugs of higher selectivity would cause fewer side effects on the blood coagulation properties of the peripheral circulation and thus potentially allow safer and more effective dosing regimens in combination therapies.

Processes that compromise the integrity of the vascular wall result in the activation of the hemostatic mechanism affecting the blood coagulation cascade and platelet activation pathways. See Furie et al., "Molecular and Cellular Biology of Blood Coagulation," *N. Eng. J Med* (1992) 326: 800–806. This response to wound repair results in the growth of a thrombus forming an occlusion that impedes the flow of blood and thus oxygen and needed nutrients to the vital tissues. For example, atherosclerosis is a disease process affecting the coronary arteries and major arterioles of the heart in which both inflammatory reactions (leukocytes, neutrophils, complement activation) and the accumulation of lipids (e.g., cholesterol, cholesterol esters, saturated fats, oxidized lipids and foam cells) occur. These events are toxic to the endothelial cells that line the blood vessel wall, the purpose of these cells being to form a protective non-thrombogenic surface or barrier separating blood from tissue. The exfoliation of the endothelial cells exposes blood to the subendothelial surface which has a high thrombogenic potential. This results in the activation of the blood coagulation cascade and the generation of active thrombin. This active thrombin becomes bound to the disease site and promotes the formation of the clot. Contact of blood with foreign surfaces such as those of extracorporeal circuits and vascular devices (stents, guidewires, etc.) also induces thrombin generation.

Thrombin converts soluble fibrinogen into insoluble fibrin at the vascular injury site where it is stabilized by enzymatic crosslinking reactions and platelet interactions. Thrombin is a potent platelet agonist and can interact on the platelet surface with receptors that lead to activation. See Furman et al, "The Cleaved Peptide of the Thrombin Receptor Is a Strong Platelet Agonist," *Proc. Natl. Acad Sci.* (1998) 95(6) :3082–3087; Zucker et al, *Platelet Activation Arteriosclerosis* (1985) 5(1):2–18. This leads to a thrombus rich in fibrin and platelets that may then become occlusive to the flow of blood to the heart and other organs such as the brain, resulting in serious life-threatening illnesses such as myocardial infarction and stroke.

There are many variations of vessel disease of the arterial and venous circulations. Clots of the arterial side tend to be enriched in platelets whereas those on the venous side contain fewer platelets and are enriched in fibrin. Thromboembolic diseases involving thrombus formation of the arterial and venous circulations include acute coronary syndromes (ACS), myocardial infarction (MI), deep vein thrombosis (DVT), pulmonary embolism (PE) and stroke to name a few. Procedures involving clamping of arteries such as carotid endarterectomy and peripheral vascular surgery also induce vascular damage, thrombin formation and platelet activation. Invasive cardiovascular procedures such as coronary artery bypass grafts (CABG), percutaneous transluminal coronary angioplasty (PTCA), cardiac catheterizations and the use of extracorporeal interventions, including cardiopulmonary bypass surgery (CPB), end-stage renal dialysis (ESRD) and extracorporeal membrane oxygenation (ECMO), potently activate the clotting system and affect platelet function.

Heparin-induced thrombocytopenia (HIT) is a special class of platelet thrombosis that occurs as an immune response to heparin, the anticoagulant drug most often employed first in the prevention and treatment of thromboembolic diseases. HIT leads to a precipitous drop in platelet count, an increase in platelet-induced thrombin generation and potentially to a fatal thrombosis. Standard treatment of HIT involves the discontinuation of heparin and use of an alternative anticoagulant such as a thrombin inhibitor, followed by close patient monitoring for the recovery of platelet counts. Despite the use of these alternatives, the morbidity and mortality of HIT patients remains high. Recently, a standard dose of GPIIb/IIIa antagonist, combined with a lowered dose of thrombin inhibitor to minimize hemorrhagic events, was used to treat HIT thrombosis. See Walenga et al, "Clinical Experience with Combined Treatment of Thrombin Inhibitors and GPIIb/IIIa Inhibitors in Patients with HIT," *Semin. Thromb. Hemost.* (1999) 25 (suppl. 1):77–81. While initial thrombosis of the coronary arteries tends to be susceptible to first treatment with fibrin-dissolving agents (e.g., tissue plasminogen activator or streptokinase), a fibrinolytic-resistant re-thrombosis often occurs that is platelet-rich. This most often requires the use of fast-acting antiplatelet drugs such as GPIIb/IIIa antagonists combined with thrombin inhibitors to control the local generation of active thrombin. However, more effective combinations of improved anticoagulants in combination with the GPIIb/IIIa antagonists are needed in the treatment of HIT and other thrombo-embolic disorders.

These improved anticoagulants require greater selectivity for thrombin at the diseased site. Surface-bound thrombin at residual levels amplifies the generation of systemic thrombin by catalyzing prothrombin consumption via the thrombin feedback loop at the site of vascular injury. See, for example, Ofosu et al, "Thrombin-Catalyzed Amplification and Inhibitory Reactions of Blood Coagulation in Thrombin: Its Key Role in Thrombogenesis-Implications for its Inhibition Clinically," *CRC Press* (1995) pp. 1–18. Moreover, when thrombin is generated in response to an injury or disease, it can be found not only in the systemic circulation or fluid phase, but is also associated with the fibrin clot, with cell surfaces such as platelets, the vessel wall and with the biomaterial surfaces of biometric circuits and devices.

Heparin affects the potent inhibition of systemic thrombin and is widely effective in the management of these thrombotic states. However, it is relatively ineffective in bringing about the inhibition of surface-bound thrombin key to the self-promotion of systemic thrombin generation. Evidence suggests that heparin may enhance clot growth when bound to the clot. See Kumar et al, "The Influence of Fibrinogen and Fibrin on Thrombin Generation-Evidence for Feedback Activation of the Clotting System by Clot Bound Heparin," *Thromb. Hemost.* (1994) 72: 713–721. Heparin's principle mode of action occurs at the level of antithrombin III (AT), a circulating proteinase inhibitor that binds thrombin and other factors of the coagulation cascade to block their activity. Heparin serves as a template to promote the assembly of the thrombin-antithrombin III complex (TAT) that then binds to exosite 2 on the surface of systemic thrombin, thereby forming a ternary complex which greatly accelerates the second order rate constant for thrombin inhibition by the serine proteinase inhibitor. However, when thrombin becomes surface-bound, such as to the fibrin clot, exosite 2 on the thrombin surface becomes unavailable to the HAT complex and surface-bound thrombin resists inhibition. Thus, recurrent thrombosis may ensue following the discontinuation of heparin therapy. See Hogg et al, "Fibrin Monomer Protects Thrombin from Inactivation by Heparin-Antithrombin III: Implications for Heparin Efficacy," *Proc. Natl. Acad. Sci. U.S.A.* (1989) 86:3619–23.

European patent application 668,875 and PCT application WO 94/09034A 1 disclose a targeted-anticoagulant concept where the efficacy of heparin to inhibit clot bound thrombin is increased by its covalent attachment to a fibrin-specific monoclonal antibody used to deliver the glycosaminoglycan (or drug) into the clot. The efficacy of this approach with respect to heparin is still limited by the unavailability of exosite 2 on clot-bound thrombin that is critical to the binding of the HAT complex. Moreover, such targeted-anticoagulant concepts do not address the catalytic thrombins that remain active and bound to surfaces such as the platelet membrane, vessel wall or biomaterial surfaces of extracorporeal circuits. Even with these targeted-anticoagulant concepts, thrombin generation can be perpetuated at other sites, causing the disease process to linger.

Clot-bound heparin is susceptible to inhibition by exosite 1 directed inhibitors such as the leech anticoagulant peptide hirudin and heparin cofactor II. See Weitz et al, "Clot-Bound Thrombin Is Protected from Inhibition by Heparin-Antithrombin III But Is Susceptible to Inactivation by Antithrombin III-Independent Inhibitors," *J. Clin. Invest.* (1990) 86: 385–391; Bendayan et al., "Dermatan Sulfate is a More Potent Inhibitor of Clot-Bound Thrombin Than Unfractionated and Low Molecular Weight Heparins," *Thromb. Haemost.* (1994) 71:576–580. However, like heparin, hirudin exhibits significant bleeding side effects associated with its use . See Kwapis et al, "Prolonged Bleeding After Cardiopulmonary Bypass with Recombinant Hirudin," *Eur. J. Cardiothorac. Surg.* (1999) 16(2):256–257; Gast et al, "Inhibition of Clot-Bound and Free (Fluid-Phase Thrombin) by a Novel Synthetic Thrombin Inhibitor (Ro 46-6240), Recombinant Hirudin and Heparin in Human Plasma," *Blood Coagul. Fibrinolysis* (1994) 5(6):879–887. Although hirudin has a marginally increased selectivity for clot-bound heparin, fluid-phase thrombin, present in significant excess, is first neutralized before completing the inhibition of the surface-bound enzyme, thus increasing anticoagulation in the systemic circulation and promoting its hemorrhagic risk potential. Attempts to reduce these side effects have been directed at improving the selectivity for inhibiting thrombin in its bound state. An inhibitor with greater selectivity for surface-bound thrombin would be predicted to have a more potent antithrombotic action and reduced effects on systemic anticoagulation. See Buchanan et al, "A Rationale for Targeting Antithrombotic Therapy at the Vessel Wall: Improved Antithrombotic Effect and Decreased Risk of Bleeding," *Wien Klin Wochenschr* (1999) 111: 81–89. This is supported by studies where the selectivity of hirudin for surface-bound thrombin was enhanced by its covalent conjugation to the anti-fibrin monoclonal antibody 59D8. See Bode et al, "Fibrin-Targeted Recombinant Hirudin Inhibits Fibrin Deposition on Experimental Clots More Efficiently than Recombinant Hirudin," *Circulation* (1994) 90(4):1956–1963; Bode et al, "Antithrombotic Potency of Hirudin Is Increased in Nonhuman Primates by Fibrin Targeting," *Circulation* (1997) 95(4):800–804. These studies support the general concept that an increased selectively for agents or drugs that target thrombin bound to surfaces would afford a greater inhibition of intravascular/extracorporeal circuit thrombosis, enhance hemostasis in the surgical wound and potentially, decrease the duration of anticoagulant therapy. Although the above utility increases the selectivity of hirudin by its covalent attachment to fibrin-specific monoclonal antibodies, it is limited to thrombin bound to the clot and does not address improvements in the inhibition of thrombin bound to platelets, vessel wall or biomaterials which perpetuate the systemic thrombotic state.

Expression of GPIIb/IIIa receptors on the surface of activated platelets greatly enhances their adhesiveness, aggregation and adherence to the fibrin clot and the injured vessel wall. See, for example, Shen et al, "Interaction of Thrombin-Activated Platelets with Extracellular Matrices (Fibronectin and Vitronectin): Comparison of the Activity of Arg-Gly-Asp-Containing Venom Peptides and Monoclonal Antibodies Against Glycoprotein IIb/IIIa Complex," *J. Pharm. Pharmacol.* (1997) 49(1):78–84. Thus thrombin-activated platelets promote thrombus growth indicating a need for improved thrombin inhibitors with antiplatelet therapies. See Eisenberg et al, "Platelet-Dependent and Procoagulant Mechanisms in Arterial Thrombosis," *Int. J. Cardiol.* (1999) 68(suppl.1):S3–S10. It is now well known that compounds that antagonize the function and/or induction of the platelet GPIIb/IIIa receptors are among the most potent antithrombotic drugs for the treatment of disease states involving platelet rich-thrombi. Indeed, these compounds inhibit platelet function or adhesion so effectively that hemorrhagic effects become a risk. See, for example, Sitges et al, "Massive Pulmonary Hemorrhage in a Patient Treated with a Platelet Glycoprotein IIb/IIIa Inhibitor," *Int. J. Cardiol.* (1997) 62(3):269–271; Gammie et al, "Abciximab and Excessive Bleeding in Patients Undergoing Emergency Cardiac Operations," *C. M. Ann. Thorac. Surg.* (1998) 65(2):465–469; Blankenship, "Bleeding Complications of Glycoprotein IIb-IIIa Receptor Inhibitors," *Am. Heart J.* (1999) 138(4 pt. 2):287–296. Moreover, depending on the clinical or experimental setting, these compounds have limited effects on thrombin generation and virtually no effect on thrombin activity. See Kleiman et al, "Inhibition of Platelet Aggregation with a Glycoprotein IIb-IIIa Antagonist Does Not Prevent Thrombin Generation in Patients Undergoing Thrombolysis for Acute Myocardial Infarction," *J. Thromb. Thrombolysis* (2000) 9(1):5–12; Dangas et al., "Effects of Platelet Glycoprotein IIb/IIIa Inhibition with Abciximab on Thrombin Generation and Activity during Percutaneous Coronary Interventions" *Am.Heart J.* (1999) 138:45–54.

The combination of thrombin inhibition therapies with platelet GPIIb/IIIa receptor therapies has been recognized as desirable in the art. See PCT applications WO 99/38827 and WO 97/35592 which disclose the inclusion of hirudin, heparin and low molecular weight heparins with a platelet GPIIb/IIIa receptor antagonist. However, the inclusion of these thrombin inhibitors can significantly contribute to the overall hemorrhagic risk. Indeed, the additivity of inhibition by the combination of heparin with GPIIb/IIIa c7E3 Fab suggests these agents may have a greater bleeding liability than the use of either agent alone. See Pedicord et al., "Glycoprotein IIb/IIIa Receptor Antagonists Inhibit the Development of Platelet procoagulant Activity," *Thromb. Res.* (1998) 90: 247–258. The therapeutic utility of lepirudin, or recombinant hirudin, is limited by its hemorrhagic potential and has shown limited benefit on thrombin generation and platelet aggregation with GPIIb/IIIa. See Koestenberger et al., "Effects of the Glycoprotein IIb/IIa Receptor Antagonist c7E3 Fab and Anticoagulants on Platelet Aggregation and Thrombin potential Under High Coagulant Challenge In Vitro," *Blood CoaguL* (2000) 11: 425–432.

There are other problems associated with heparin and hirudin use, including antigenic reactions. Anti-hirudin antibodies are elicited in 74% of the recipients and is contraindicated in patients with a known hypersensitivity to this anticoagulant. Huhle et al, "Immunologic Response to Recombinant hirudin in HIT Type II Patients during Long-Term Treatment," *Br. J. Haematol.* (1999) 106(1):195–201 (appendix U); Gollnick, "Allergy to Heparin, Heparinoids, and Recombinant Hirudin: Diagnostic and Therapeutic Alternatives," *Hautarzt* (1999) 50(6):406–411. The lack of an antidote to hirudin and other thrombin inhibitors may necessitate transfusion as the only option to remedy adverse events.

Heparin-induced thrombocytopenia type II (HIT) is a consequence of heparin exposure, especially in situations such as CPB where high doses of heparin are required to manage high levels of thrombin that are continually produced during and after clinical procedures are performed. See Brister et al, "Thrombin Generation during Cardiac Surgery: Is Heparin the Ideal Anticoagulant?," *Thromb. Haemostas.* (1993) 70(2):259–262; Bauer et al, "Prevalence of Heparin-Associated Antibodies without Thrombosis in Patients Undergoing Cardiopulmonary Bypass Surgery," *Circulation* (1997) 95:1242–1246; Pouplard et al, "Antibodies to Platelet Factor 4-Heparin After Cardiopulmonary Bypass in Patients Anticoagulated with Unfractionated Heparin or a Low Molecular Weight Heparin: Clinical Implications for Heparin-Induced Thrombocytopenia," *Circulation* (1999) 99:2539–2536; Trossaert et al, "High Incidence of Anti-Heparin/Platelet Factor 4 Antibodies After Cardiopulmonary Bypass surgery," *Br. J. Haematol.* (1998) 101(4) :653–655. The bleeding problems associated with heparin use during CPB requires its neutralization by protamine salts post-CPB; this enhances the activation of inflammatory mediators, such as complement and proinflammatory cytokines which complicate outcome. See Morel et al, "C5a and Thromboxane Generation Associated with Vaso-and Broncho-Constriction During Protamine Reversal of Heparin," *Anesthesiology* (1987) 66(5):597–604; Fehr et al, "In Vivo Complement Activation by Polyanion-Polycation Complexes: Evidence that C5a Is Generated Intravascularly During Heparin-Protamine Interaction," *Clin. Immunol. Immunopathol.* (1983) 29(1):7–14. Thrombin rebound (i.e., the inability of the HAT complex to neutralize trace levels of thrombin deposited on surfaces, such as the CPB circuit, surgical wound, etc.) can also occur, predisposing the patient to increased risk of thrombosis.

Accordingly, it would be desirable to be able to provide the combination of an improved thrombin inhibition therapy that provides sustained inhibition of catalytic thrombins bound to surfaces with a platelet GPIIb/IIIa receptor therapy that minimizes or prevents undesired hemorrhagic side effects, as well as potential antigenic reactions.

SUMMARY OF THE INVENTION

The present invention relates to pharmaceutical combinations that can inhibit thrombin generation and platelet aggregation with minimized or reduced hemorrhagic properties and high selectivity for surface-bound thrombin inhibition. These combinations comprise:

(a) a heparin cofactor II agonist; and
(b) a platelet glycoprotein (GP)IIb/IIIa receptor antagonist;
(c) the amount of a heparin cofactor II agonist and the amount of the platelet GPIIb/IIIa receptor antagonist combined being therapeutically effective to inhibit thrombin generation and platelet aggregation.

The present invention further relates to methods for inhibiting platelet aggregation and thrombin generation, which comprises the step of: administering (as a combined dose or as separate related doses) to a mammal in need thereof (e.g., to prevent and/or treat a variety of thrombo-embolic disorders) a combined therapeutically effective amount of a heparin cofactor II agonist and a platelet (GP) IIb/IIIa receptor antagonist.

It has been found that the administration of a combined therapeutically effective amount of a heparin cofactor II agonist or activating substance with a platelet GPIIb/IIIa receptor antagonist can provide a superior therapeutic effect in inhibiting platelet aggregation and thrombin generation (especially thrombin generation due to surface bound thrombin) than either component alone, or prior combinations of a platelet GPIIb/IIIa receptor antagonist with either unfractionated heparin, low molecular weight heparins or hirudin. Indeed, it has been found that subtherapeutic amounts of a heparin cofactor II agonist activating substance can be combined with subtherapeutic amounts of a platelet (GP) IIb/IIIa receptor antagonist to provide a therapeutically effective benefits in inhibiting platelet aggregation and thrombin generation. These surprising therapeutic benefits can be achieved while at the same time minimizing or reducing the risk of hemorrhagic side effects (e.g., prolonged bleeding), and without causing undesired antigenic responses.

DETAILED DESCRIPTION OF THE INVENTION

As used herein, the terms "therapeutic amount" and "therapeutically effective amount" mean that the dosage or amount of the particular compound, drug or pharmaceutical agent is sufficient to achieve the desired pharmacological action.

As used herein, the term "subtherapeutic amount" means that the dosage or amount of a particular compound, drug or pharmaceutical agent is insufficient to achieve the desired pharmacological action in the absence of other compounds, drugs or pharmaceutical agents. Subtherapeutic amounts and doses will usually not be less than about 5%, typically not less than about 10%, and typically not greater than about 75%, more typically not greater than about 60%, of the therapeutic dosage or amount.

As used herein, the term "pharmaceutically acceptable salt" means non-toxic salts of the compounds (which are generally prepared by reacting the free acid with a suitable organic or inorganic base) and include, but are not limited to, the acetate, benzenesulfonate, benzoate, bicarbonate, bisulfate, bitartrate, borate, bromide, calcium, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabarnine, hydrobromide, hydrochloride, hydroxynapthoate, iodide, isothionate, lactate, lactobionate, laurate, malate, maleate, mandlate, mesylate, methylbromide, methylnitrate, methylsulfate, mucate, napsylate, nitrate, oleate, oxalate, pamaote, palmitate, panthothenate, phosphate, diphospate, polygalacturonate, salicylate, stearate, subacetate, succinate, tannate, tartrate, teoclate, tosylate, triethiodide, and valerate salts, as well as mixtures of these salts.

As used herein, the terms "active ingredient," "active component," "active drug," and "drug" are used interchangeably to refer to the heparin cofactor II agonist, the platelet GPIIb/IIIa receptor antagonist or both.

As used herein, the term "mammal" includes primates (e.g., humans, monkeys, etc.), dogs, rabbits, rats, mice and other species commonly known to be mammals.

As used herein, the term "comprising" means various components and steps can be conjointly employed in the present invention. Accordingly, the term "comprising" encompasses the more restrictive terms "consisting essentially of" and "consisting of."

All amounts, parts, ratios and percentages used herein are by weight unless otherwise specified.

A key active ingredient or component of the combinations of the present invention is a heparin cofactor II (HCII) agonist. As used herein, an HCII agonist (also referred to hereafter interchangeably as an "HCII activating substance") is a compound (typically a sulfated polysaccharide) that binds to HCII and enhances its intrinsic thrombin inhibitory action without the direct interaction of the agonist with thrombin (i.e., by allosteric activation). See Buchanan et al, "Evidence for a Conformational Change of Surface-Bound Thrombin That Promotes Vessel Wall Thrombogenicity: Selective and Sustained Inhibition of Its (Surface-Bound Thrombin) by Intimatan (DS)/HCII," *Thromb. Haemost.* (2001, In Press). HCII is a natural inhibitor of thrombin ubiquitously present in tissues and the circulation. Like antithrombin III (AT), it is an endogenous proteinase inhibitor of the circulatory system but it is also present in extravascular tissues. However, and unlike AT, HCII specifically inhibits thrombin and not other proteases of the coagulation cascade. By a process somewhat analogous to hirudin, HCII inhibits clot-bound thrombin by first binding to exosite 1 allowing its C-terminal inhibitory domain to react with the active site. See, for example, Hortin et al, "Antithrombin Activity of a Peptide Corresponding to Residues 54–75 of Heparin Cofactor II," *J. Biol. Chem.* (1989) 264(24):13979–13982; Van Deerlin et al, "The N-Terminal Acidic Domain of Heparin Cofactor II Mediates the Inhibition of Alpha-Thrombin in the Presence of Glycosaminoglycans," *J. Biol. Chem.* (1991) 266(30) :20223–20231. However, and unlike hirudin, HCII assumes a latent state in vivo such that its thrombin inhibitory activity can be switched on by a second molecule, such as dermatan sulfate (to be discussed hereafter.). See Tollefsen et al, "Activation of Heparin Cofactor II by Dermatan Sulfate," *J. Biol. Chem.* (1983) 258(11):6713–6716.

Some representative but nonlimiting examples of HCII activating substances suitable for use in the present invention include various sulfated polysaccharides such as dermatan sulfate (and various oversulfated derivatives thereof), sulfated polysaccharides derived from sea cucumber, sulfated polysaccharides derived from green algae and PI-88, a sulfated pentomannose, and their pharmaceutically acceptable salts. See U.S. Pat. No. 5,922,690 (Van Gorp et al), issued Jul. 13, 1999; U.S. Pat. No. 5,993,797 (Kitazato et al), issued Nov. 30, 1999; Hayakawa et al., "Inhibition of Thrombin by Sulfated Polysaccharides Isolated from Green Algae," *Biochim. Biophys. Acta* (2000) 30: 86–94; Demir et al., "Ecarin Clotting Time is Sensitive to Heparinoids: Comparison of Two different Techniques," *Clin. Appl. Thromb. Hemost.* (2001) 7: 38–43, all of which are incorporated by reference.

Combinations of the present invention that are particularly useful are those where the HCII activating substance is dermatan sulfate and its oversulfated derivatives. Dermatan sulfate offers significant advantages relative to the other thrombin inhibitors that have lower selectivity for bound thrombin and thus higher hemorrhagic potentials. It is also advantageous and superior to conjugates of these thrombin inhibitors even when they are bound to targeting agents such as monoclonal antibodies. Dermatan sulfate is particularly advantageous as it more effectively subdues thrombin activity associated with all surfaces, thus lowering the overall systemic thrombogenic potential including the activation of platelets due to inhibition of thrombin associated with the platelet surface. When used in conjunction with a platelet GPIIb/IIIa receptor antagonist, dermatan sulfate is especially beneficial in permitting lower concentrations of the GPIIb/IIIa antagonist to be used to achieve the same and/or superior anti-thrombotic effects with lower risk of bleeding side-effects than if either agent were used alone.

The dermatan sulfates useful in the present invention have more than about 25%, preferably more than about 50%, repeating L-iduronic acid→4,6-di-O-sulfated N-acetyl-D-galactosamine disaccharide units, and typically having a molecular weight of from about 1,000 Daltons to about 60,000 Daltons. Particularly preferred dermatan sulfates useful in the present invention are oversulfated derivatives that have more than about 75%, preferably more than about 90%, repeating L-iduronic acid→4,6-O-disulfated-N-acetyl-D-galactosamine disaccharide units, and are disclosed in U.S. Pat. No. 5,922,690 (Van Gorp et al), issued Jul. 13, 1999, which is incorporated by reference. These preferred oversulfated dermatan sulfates (hereinafter referred to as "dermatan disulfate" or "DDS") comprise a mixture of dermatan polymeric chains principally containing connected disulfated disaccharide dimers obtained by chemical sulfation of native dermatan sulfate (primarily L-iduronic acid→N-acetyl-D-galactosamine-4-O-sulfate) that comprises primarily repeating L-iduronic acid→N-acetyl-D-galactosamine-4,6-O-disulfated disaccharide units. Preferably, DDS has an average molecular weight in the range of from about 2,500 to about 37,500 Daltons, preferably from about 5,000 to about 30,000 Daltons, corresponding to from about 6 to about 100 monosaccharide units in the polymeric chains. The DDS having an average molecular weight less than about 30,000 Daltons is preferably obtained by cleaving longer chain polysaccharides of: (1) native dermatan sulfate (hereinafter referred to as "native DS") followed by site-specific sulfation of the N-acetyl-D-galactosamine 4-O-sulfate ring at the 6-O hydroxyl to yield primarily the 4,6-O-disulfated disaccharide, or (2) by depolymerization of the DDS. Dermatan chains can be depolymerized by a variety of enzymatic and chemical methods known to those skilled in the art, including those disclosed in U.S. Pat. No. 5,922,690, supra.

The preferred DDS useful in the present invention has significant AT-independent antithrombin activity mediated through the action of HCII and can be synthesized from commercially obtained DS or preferably native DS according to methods disclosed in U.S. Pat. No. 5,922,690, supra. The preferred DDS can be in the form of a salt, where the cation is selected from barium, calcium, copper, lithium, sodium, potassium, zinc, and ammonium ions. See U.S. Pat. No. 5,922,690, supra.

Another active ingredient or component of the combinations of the present invention is a platelet GPIIb/IIIa receptor antagonist. The platelet GPIIb/IIIa antagonists include a variety of antibody, antibody fragments, peptides and small molecule compounds that effectively inhibit the expression and/or function of platelet GPIIb/IIIa receptors, as well as their pharmaceutically acceptable salts. Some representative but nonlimiting examples of platelet GPIIb/IIIa antagonists suitable for use in the present invention include various peptides, such as those disclosed in U.S. Pat. Nos. 5,470,894, 5,463,011, 5,455,243, 5,451,578, 5,446,056, 5,441,952, 5,422,249, 5,416,099, 5,405,854, 5,397,791, 5,393,670, 5,389,631, 5,380,713, 5,374,622, 5,353,956, 5,344,783, 5,340,798, 5,338,723, 5,334,596, 5,321,034, and 5,318,899 (e.g. cyclic heptapeptides Mpr-(Acetimidyl-Lys)-Gly-Asp-Trp-Phe-Cys-NH$_2$, Mpr-(Acetimidyl-Lys)-Cly-Asp-Trp-Phe-Pen-NH$_2$, Mpr-(Phenylimidyl-Lys)-Gly-Asp-Trp-Phe-Pen-NH$_2$, and Mpr-(Phenylimidyl-Lys)-Gly-Asp-Trp-Phe-cys-NH$_2$, where Mpr is mercapto propionyl), and various nonpeptide compounds such as those disclosed in U.S. Pat. Nos. 5,312,923, 5,294,616 and 5,292,756 (e.g., 2-S(n-butylsulfonylamino)-3[4-(piperidin-4-yl)butyloxyphenyl]propionic acid and 2-S(n-butylsulfonylamilino)-[4-(piperidin-4-yl)buteloxyphenyl]propionic acid hydrochloride), those disclosed in U.S. Pat. Nos. 5,281,585 5,272,158, 5,264,420, 5,260,307, and 5,239,113 (e.g., ethyl 3-[[4-[[4-(aminoiminomethyl)phenyl]amino]-1,4-dioxobutyl]amino]-4-pentynoate), disclosed in U.S. Pat. Nos. 5,227,490, 5,206,373, and 4,703,036 (e.g., N-methyl-D-phenylalanyl-N-[(1S)-1-formyl-4-guanidinobutyl]-L-prolinamide), those disclosed in European Patent Document 505,868 (e.g., ((1-(2-((4-piperidinyl)oxy)-(S)-acetic acid), those disclosed in PCT application WO 93/11152 (e.g., N-(2-(2-(((3-((aminoiminomethyl)amino)propyl)amino)-carbonyl)-1-piperidnyl)-1-(cyclohexylmethyl)-2-oxoethyl)-(R,S)-glycine), and those disclosed in European patent application 333,356 and PCT applications WO 94/22820, WO 95/14683 and 94/18981, all of which are incorporated by reference. See also U.S. Pat. Nos. 5,976,532, 5,952,306, 5,968,902, 6,001,961, 6,008,193, 5,731,324, 6,022,523, 6,020,362 and 6,013,625, all of which are incorporated by reference. Preferred platelet GPIIb/IIIa antagonists suitable for use in the present invention include [3(R)-[2-piperidin-4-yl)ethyl]-2-piperidone-1]acetyl-3(R)-methyl-b-alanine, 2(S)-[(p-toluenesulfonyl)amino]amino]-3-[[[5,6,7,8-tetrahydro-4-oxo-5-[2-(piperidin-4-yl)ethyl]-4H-pyrazolo-[1,5-a][1,4]diazepin-2-yl]carbonyl]-amino]propionic acid, 5-[(4-piperidinyl)methoxy]-2-indolecarbonyl-2(S)-phenylsulfonyl-amino-b-alanine, 2-S-(n-butylsulfonylamnino)-3[4-piperdin-4-yl)butyloxyphenyl] propionic acid hydrochloride (also known as tirofiban), (R)-methyl-3-[[[3-[4-(aminoiminomethyl)phenyl]-4,5-dihydro-5-isoxazolyl]acetyl]amino]-N-(butoxycarbonyl)-L-alanine monoacetate (DMP 754), RO44-9883 and RO43-8857 from Hoffman-LaRoche, xemlofiban (also know as xemilofiban) from Searle/Sankyo, fradafiban from Boehringer Ingleheim/K. Thomae, SB 2144856 from Smith-Kline Beecham, ZD2486 from Zeneca, TAK 029 from Takeda, orbofiban and SC-58635 from Searle, GR144053 from Glaxo, compound 109891 from Rhone Poulenc Rorer (now Aventis), and sibrafiban from Hoffman-LaRoche, as well as mixtures thereof. See PCT application WO 99/38827 (Cook et al), published Aug. 5, 1999, which is incorporated by reference. Other preferred platelet GPIIb/IIIa antagonists suitable for use in the present invention include Integrilin® (also known as eptifibatide of Cor Therapeutics), a cyclic heptapeptide inhibitor with an active pharmiacophore derived from the structure of barbourin from the venom of the southeastern pigmy rattlesnake. See Phillips et al., "Clinical Pharmacology of Eptifibatide" Am. J. Cardiol. (1997):11B–20B and related compouids disclosed in U.S. Pat. Nos. 5,968,902, 5,958,732, 5,935,926, 5,851,839, 5,843,897, 5,807,828, 5,807,825, 5,795,868, 5,795.867, 5,786,333, 5,780,595, 5,759,999, 5,756,451, 5,686,571, 5,686,570, 5,686,569, 5,686,568, 5,686,567, 5,686,566, and 5,344,783, all of which are incorporated herein by reference. Mixtures of these or preferred platelet GPIIb/IIIa antagonists can also be used in the present invention.

A particular advantage of using combinations of the heparin cofactor II agonist and the platelet GPIIb/IIIa receptor antagonist to inhibit platelet aggregation and thrombin generation is that a therapeutically effective amount of either active ingredient is necessarily not required to achieve the desired therapeutic effect. While the present invention encompasses combined use (and combinations) of the heparin cofactor II agonist and a platelet GPIIb/IIIa receptor antagonist where each is in a therapeutically effective amount, therapeutically effective amounts of each active ingredient are not necessarily required to inhibit platelet aggregation and thrombin generation. Indeed, it has been found that subtherapeutic amounts of either or both active ingredients can be used so long as the amount of each active ingredient, when used in combination, achieves the desired therapeutic effect.

The present invention can be in the form of injectable or oral compositions for administering HCII agonists and platelet GPIIb/IIIa receptor antagonists. Suitable injectable compositions for use in the present invention can be given intravenously, parenterally, intramuscularly, or subcutaneously and include bolus or extended infusion compositions. Injectable compositions suitable for use in the present invention are well known to those skilled in the pharmaceutical arts. The HCII agonists and platelet GPIIb/IIIa receptor antagonists can be administered to the patient together, i.e., as a combined dose in one composition, or can be administered separately to the patient, i.e., as separate doses of HCII agonists and platelet GPIIb/IIIa receptor antagonists in different compositions that are administered simultaneously, concurrently or otherwise sufficiently close in time to provide the desired therapeutic benefit. Injectable administration of HCII agonists and platelet GPIIb/IIIa receptor antagonists according to the present invention, whether administered together as one dose or composition, or as separate doses or compositions, typically involves the preparation of suitable infusion solutions according to procedures well known to those skilled in the pharmaceutical arts. Administration in theses various ways are suitable for the present invention as long as the beneficial pharmaceutical effect of the HCII agonists and platelet GPIIb/IIIa receptor antagonists is realized by the patient. Such beneficial effect is usually achieved when the target plasma level concentrations of each active drug are maintained at substantially the same time. Such target plasma level concentrations are readily determined for each patient by physicians and veterinarians skilled in the art.

The dosage regimen for the active ingredients is selected in accordance with a variety of factors, including type, species, age, weight, sex and medical condition of the patient; the severity of the condition to be treated or prevented; the routes of administration; the renal and hepatic function of the patient; and the particular HCII agonist and platelet GPIIb/IIa receptor antagonist to be used. An ordinarily skilled physician or veterinarian can be readily determine and prescribe the therapeutically effective amount of the combined active ingredients required to prevent, counter, or arrest the progress of the condition. For example, in the case of the preferred HCII agonist DDS, therapeutic doses will typically be in the range of from about 0.1 to about 5 mg/kg. (as an intravenous bolus), followed by a maintenance intravenous infusion of from about 5 to about 30 microg/kg/min. Subtherapeutic doses of DDS that can be useful in the combinations according to the present invention will typically be in the range of from about 0.01 to 0.1 mg/kg. (as an intravenous bolus), followed by a maintenance intravenous infusion of from about 0.5 to about 5 microg/kg/min. With regard to the platelet GPIIb/IIIa receptor antagonist, for example, tirofiban, therapeutic doses for treating unstable angina pectoris can be administered intravenously at an initial infusion rate of from about 0.2 to about 1 microg/kg/min. for 30 minutes or 10 microg/kg/min. over 3 minutes, followed by a maintenance infusion dose of from about 0.1 to about 1 microg/kg/min.; for treating angioplasty/artherectomy, an initial intravenous infusion in the range of from about 3 to about 30 microg/kg/min. over 3 minutes, followed by a maintenance dose at the rate of from about 0.1 to about 1 microg/kg/min. Subtherapeutic doses of tirofiban that can be useful in the combinations according to the present invention for treating unstable angina pectoris are typically be administered intravenously at an initial infusion rate of from about 0.02 to about 0.1 microg/kg/min. for 30 minutes or from about 0.1 to about 1 microg/kg/min. over 3 minutes, followed by a maintenance infusion dose of from about 0.01 to about 0.1 microg/kg/min.; for treating angioplasty/artherectomy, an initial intravenous infusion in the range of from about 0.3 to about 3 microg/kg/min. over 3 minutes, followed by a maintenance dose at the rate of from about 0.01 to about 0.1 microg/kg/min.

The active ingredient can be administered in admixture with suitable pharmaceutical diluents, excipients or carriers (collectively referred to hereinafter as "pharmaceutical carriers") suitable selected with respect to the intended form of administration, that is oral tablets, capsules, elixirs, syrups and the like, and consistent with conventional pharmaceutical practices. Typically, suitable injectable (e.g., intravenous) solutions include pharmaceutically acceptable pH buffers (e.g., sodium citrate), tonicity adjusting agents and other components providing a storage stable and therapeutically effective injectable solution. Tonicity adjusting agents, including sodium chloride, are used to adjust tonicity for osmotic pressure and to prevent blood cell lysing. These agents minimize pain and thrombophlebitis often experienced by patients receiving intravenous administrations of pharmaceutical compositions. The amount used is that which makes the formulation isotonic with the osmotic pressure of the biological system of the patient. Expressed in osmolarity units, the preferred amounts of tonicity adjusting agent suitable for use in the present invention (e.g., sodium chloride) are from about 50 to about 500 milliosmoles, more preferably about 290 milliosmoles. In compositions of the present invention, pharmaceutically acceptable osmolarity can be achieved by formulating with an amount of sodium chloride of from about 1.5 to about 15 mg/ml, preferably about 9 mg/m. Such osmolality can also be achieved by using an amount of mannitol of from about 7 to about 75 mg/ml, preferably about 50 mg/ml. Other tonicity adjusting agents which can be used to adjust tonicity include, but are not limited to, dextrose and other sugars. The formulations according to the present invention can also be suitable for long-term storage in glass containers commonly used in the pharmaceutical industry, e.g., in concentrated form in standard USP Type * borosilicate glass containers.

In general, the method for preparing compositions of the present invention comprising the active ingredients (i.e., HCII agonist, platelet GPIIb/IIIa receptor antagonist or both) involves combining the various ingredients in a mixing vessel, e.g., at room temperature. The active ingredients (in salt or free base form), buffers sources (e.g., citric acid and sodium citrate), and tonicity adjusting agent(s), are combined to obtain an active ingredient concentration typically in the range of from about 0.01 mg/ml to about 1 mg/ml. In one embodiment for preparing such compositions, a substantial portion of the finished product amount of water (for example, from about 60 to 100%) is introduced into a standard pharmaceutical mixing vessel. An amount of the active ingredients suitable for obtaining the desired finished product concentration is dissolved in the water. Amounts of sodium citrate and citric acid sufficient to obtain a finished citrate concentration of from about 2 to about 20 mM, are added. A pharmaceutically acceptable amount of tonicity adjusting agent in the isotonic range is added. Any remaining portion of water is then added to achieve the desired final concentrations of ingredients. The amount of water initially used in preparing the formulation, and the amount of the remaining portion of water added at the end of the procedure, does not affect the properties of the finished product. Such amounts are a matter of choice for those skilled in the pharmaceutical arts, allowing for pH adjustment during formulation. Concentrated formulations of the compositions of the present invention can be diluted at the time of administration with a suitable diluent to obtain a finished concentration, for example, of about 0.05 mg/ml, which is suitable for transfer to an infusion bag and use by a patient in need of the treatment.

HCII agonists and/or platelet GPIIb/IIIa receptor antagonists that are orally active can be administered as oral dose forms one or more times during the day, e.g., one, two, three or four times daily. For oral administration in the form of a tablet or capsule, the active ingredient (i.e., the HCII agonists, the platelet GPIIb/IIIa receptor antagonist or both) can be combined with an oral, non-toxic pharmaceutically acceptable, inert carrier such as lactose, starch, sucrose, glucose, methyl cellulose, magnesium stearate, dicalcium phosphate, calcium sulfate, mannitol, sorbitol and the like. For oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or β-lactose, corn-sweeteners, natural and synthetic gums such as acacia, tranacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

Oral compositions with enteric coatings can be prepared by mixing the active ingredient with an excipient to form a spheroid, and coating the spheroid with a thin polymer film. For example, the active ingredient can be mixed with non-water swellable microcrystalline cellulose to form a spheroid which is then coated with a film of hydroxypropyl methyl cellulose phthalate and or a plasticizer which prevents any release of the active ingredient in the stomach. When the composition reaches the intestine, the active ingredient is then released. Other suitable materials for enteric coatings include, for example, hydroxypropyl methyl cellulose acetate succinate, hydroxypropyl methyl cellulose hexahydrophthalate, shellac, cellulose acetate, cellulose acetate phthalate, polyvinyl acetate phthalate, carboxymethyl ethyl cellulose, methacrylic acid copolymers, methacrylic ester copolymers and the like.

Oral compositions can also be prepared by mixing the active ingredient with a wetting agent such as fatty acid esters, lecithin, sucrose, mannitol or sorbitol and then spheronizing or granulating the mixture into microgranules. These are then coated with a microporous membrane polymer such as Eudragit® E30D (Rohm Pharma GmbH, Weiterstadt, Germany), hydroxypropyl methyl cellulose phthalate and other wetting agents, plasticizers and the like. These formulation are enteric by nature and the active ingredient does not become bioavailable until the system reaches the intestine.

Oral compositions can also be prepared by mixing the active ingredient and an acid such as fumeric or tartaric acid which is compressed into a spherical tablet and coated with lacquers that are insoluble in gastric juices but soluble in intestinal juices. These lacquers include copolymers of acrylic acid and methacrylic acid esters. The acidic matrix prevents quick dissolution early and yet promotes the active ingredient's bioavailability further downstream in the digestive tract.

Oral compositions can also be prepared by coating a solid dosage form of the active ingredient with hydroxypropyl methyl cellulose phthalate or acidic succinyl and acetyl esters of hydroxypropyl methyl cellulose. Triethylcitrate is added as a plasticizer which aids in the binding of the coating material to the core pellet. The coating resists dissolution in the stomach but completely dissolves in the small intestine.

In general, solid dosage forms comprising the active ingredient can be coated using conventional coating techniques such as conventional pan coating techniques or column spray coating techniques. See PCT application WO 99/38827 (Cook et al), published Aug. 5, 1999 (herein incorporated by reference) for a more detailed description of these techniques.

The active ingredients can also be administered in the form of liposome delivery systems, such as small unilamellar vesicles, large unilamellar vesicles and multilamellar vesicles. The liposomes can be formed from a variety of phospholipids, such as cholesterol, stearylarnine or phophatidylcholines.

The active ingredients can also be delivered using monoclonal antibodies as individual carriers to which the active ingredient molecules are coupled or the active ingredients can be coupled with soluble polymers as targetable drug carriers. These soluble polymers include polyvinylpyrrolidone, pyran copolymer, polyhydroxypropyl-methacrylamide-phenol, polyhydroxy-ethyl-aspartamide-phenol, or polyethyleneoxide-polylysine substituted with palmitoyl residues. In addition, the active ingredients can be coupled to biodegradable polymers that control the release of the active ingredient, for example, polylactic acid, polyglycolic acid, copolymers of polylactic and polyglycolic acid, polyepsilon caprolactone, polyhydroxy butyric acid, polyorthoesters, polyacetals, polydihydropyrans, polycynacrylates and cross-linked or amphiphatic block copolymers of hydrogels.

The active ingredients can also be formulated as ocular eye drops. See PCT application WO 99/38827 (Cook et al), published Aug. 5, 1999 (herein incorporated by reference) for a more detailed description of the other ingredients in ocular eye drop formulations, suitable dosing schemes for such formulations and methods for preparing such formulations. Suitable eyedrop formulations are those which are isotonic and maintain sufficient contact with the eye surface to systemically deliver the active ingredient to the patient. The ocular preparation can be a solid insert, such as one which, after dispensing the active ingredient, remains essentially intact, or a bioerodible insert that is soluble in lacrimal fluids, or otherwise disintegrates. See PCT application WO 99/38827 (Cook et al), published Aug. 5, 1999 (herein incorporated by reference) for a more detailed description of solid insert embodiments. The ocular preparation can also be in the form of an ointment which is compounded, for example, by mixing finely milled powdered ingredients with a small amount of petrolatum (e.g., white petrolatum) and levigating or otherwise mixing until a uniform distribution is achieved with the balance of the petrolatum being added by geometric addition until the desire dosage form is made.

The active ingredients can also be formulated for intranasal delivery. See Mousa et al, "Intranasal Antiplatelet/Antithrombotic Efficacy of a Novel Platelet GPIIB/IIIA Receptor Antagonist DMP755," *Thromb. Res.* (1998) 92:115–124, which is incorporated by reference.

The HCII agonists and a platelet GPIIb/IIIa receptor antagonists when administered as a combined dosage or when administered as separate dosages in combination can be used to prevent, moderate, minimize, reduce or otherwise treat a variety of disease states or conditions that require inhibition of platelet aggregation and thrombin generation. The combined use of heparin cofactor II agonists and a platelet GPIIb/IIIa receptor antagonists according to the present invention is especially beneficial where the risk of hemorrhagic side effects (e.g., prolonged bleeding) and potential antigenic responses need to be avoided or at least minimized.

The combined use of HCII agonists and a GPIIb/IIIa receptor antagonists according to the present invention can be used to treat or prevent various arterial and venous thrombo-embolic disorders and disease states. Disorders and disease states that the present invention can be useful in treating or preventing include, but are not limited to, acute coronary syndromes (e.g., angina), myocardial infarction, pulmonary embolism, deep vein thrombosis, stroke, as well as antigenic reactions or responses caused by heparin, hirudin and other similar derivatives, such as heparin-induced thrombocytopenia (the allergic reaction caused by treatment with heparin).

The combined use of HCII agonists and a platelet GPIIb/IIIa receptor antagonists according to the present invention can be used to various clinical or surgical procedures where platelet aggregation and thrombin generation can be a potential problem. These procedures include but are not limited to cardiopulmonary bypass surgery, extracorporeal membrane oxygenation procedures, coronary artery bypass graft surgery, percutaneous transluminal coronary angiography procedures (e.g., where stent thrombosis is a particular problem), and similar procedures.

While specific embodiments of the present invention have been described, it will be apparent to those skilled in the art that various modifications thereto can be made without departing from the spirit and scope of the present invention as defined in the appended claims.

What is claimed is:

1. A pharmaceutical combination, which comprises:
   (a) a heparin cofactor II agonist; and
   (b) a platelet GPIIb/IIIa receptor antagonist;
   (c) the amount of a heparin cofactor II agonist and the amount of the platelet GPIIb/IIIa receptor antagonist combined being therapeutically effective to inhibit thrombin generation and platelet aggregation.

2. The combination of claim 1 wherein heparin cofactor II agonist is a sulfated polysaccharide.

3. The combination of claim 2 wherein the sulfated polysaccharide is dermatan sulfate having more than about 25% repeating L-iduronic acid→4,6-di-O-sulfated N-acetyl-D-galactosamine disaccharide units.

4. The combination of claim 3 wherein the dermatan sulfate has more than about 50% repeating L-iduronic acid→4,6-di-O-sulfated N-acetyl-D-galactosaminie disaccharide units.

5. The combination of claim 3 wherein the dermatan sulfate has a molecular weight of from about 1,000 Daltons to about 60,000 Daltons.

6. The combination of claim 5 wherein the dermatan sulfate has more than about 75% repeating L-iduronic acide→4,6-di-O-sulfated N-acetyl-D-galactosamine disaccharide units.

7. The combination of claim 5 wherein the dermatan sulfate has a molecular weight of from about 2,500 to about 37,500 Daltons.

8. The combination of claim 3 wherein the platelet GPIIb/IIIa receptor antagonist is a cyclic heptapeptide selected from the group consisting of Mpr-(Acetimidyl-Lys)-Gly-Asp-Trp-Phe-Cys-NH$_2$, Mpr-(Acetimidyl-Lys)-Cly-Asp-Trp-Phe-Pen-NH$_2$, Mpr-(Phenylimidly-Lys)-Gly-Asp-Trp-Phe-Pen-NH$_2$, and Mpr-(Phenylimidyl-Lys)-Gly-Asp-Trp-Phe-Cys-NH$_2$, wherein Mpr is mercapto propionyl.

9. The combination of claim 3 wherein the platelet GPIIb/IIIa receptor antagonist is selected from the group consisting of [3(R)-[2-piperidin-4yl)ethyl]-2-piperidone-1]acetyl-3(R)-methyl-b-alanine, 2(S)-[(p-toluenesulfonyl)amino]amino]-3-[[[5,6,7,8-etrahydro-4-oxo-5-[2-(piperidin-4-yl)ethyl]-4H-pyrazolo-[1,5-a][1,4]diazepin-2-yl]carbonyl]-amino]propionic acid, 5-[(4-piperidinyl)methoxy]-2-indolecarbonyl-2(S)-phenylsulfonyl-amino-b-alanine, 2-S-(n-butylsulfonylamino)-3[4-piperdin-4-yl)butyloxypheyl]propionic acid hydrochloride, (R)-methyl-3-[[[3-[4-(aminoiminomethyl)phenyl]-4,5-dihydro-5-isoxazolyl]acetyl]amino]-N-(butoxycarbonyl)-L-alanine monoacetate, xemlofiban, orbofiban, eptifibatide and mixtures thereof.

10. The combination of claim 1 wherein the amount of at least one of the heparin cofactor II agonist and the platelet GPIIb/IIIa receptor antagonist is a subtherapeutic amount.

11. The combination of claim 10 wherein the amount of each of the heparin cofactor II agonist and the platelet GPIIb/IIIa receptor antagonist is a subtherapeutic amount.

12. A method for inhibiting platelet aggregation and thrombin generation, which comprises the step of administering to a mammal in need thereof a combined therapeutically effective amount of a heparin cofactor II agonist and a platelet GPIIb/IIIa receptor antagonist.

13. The method of claim 12 wherein the heparin cofactor II agonist and the platelet GPIIb/IIIa receptor antagonist are each administered as separate doses.

14. The method of claim 12 wherein the heparin cofactor II agonist and the platelet GPIIb/IIIa receptor antagonist are administered as a combined dose.

15. The method of claim 12 wherein the amount administered of at least one of the heparin cofactor II agonist and the platelet GPIIb/IIIa receptor antagonist is a subtherapeutic amount.

16. The method of claim 15 wherein the amount administered of each of the heparin cofactor II agonist and the platelet GPIIb/IIIa receptor antagonist is a subtherapeutic amount.

17. The method of claim 12 wherein the heparin cofactor II agonist is a dermatan sulfate having more than about 25% repeating L-iduronic acid→4,6-di-O-sulfated N-acetyl-D-galactosamine disaccharide units and wherein the platelet glycoprotein IIB/IIIA receptor antagonist is selected from the group consisting Mpr-(Acetimidyl-Lys)-Gly-Asp-Trp-Phe-Cys-NH$_2$, Mpr-(Acetimidyl-Lys)-Cly-Asp-Trp-Phe-Pen-NH$_2$, Mpr-(Phenylimidyl-Lys)-Gly-Asp-Trp-Phe-Pen-NH$_2$, and Mpr-(Phenylimidly-Lys)-Gly-Asp-Trp-Phe-Cys-NH$_2$, wherein Mpr is mercapto propionyl, [3(R)-[2-piperidin-4yl)ethyl]-2-piperidone-1]acetyl-3(R)-methyl-b-alanine, 2(S)-[(p-toluenesulfonyl)amino]amino]-3-[[[5,6,7,8-etrahydro-4-oxo-5-[2-(piperidin-4-yl)ethyl]-4H-pyrazolo-[1,5-a][1,4]diazepin-2-yl]carbonyl]-amino]propionic acid, 5-[(4-piperidinyl)methoxy]-2-indolecarbonyl-2(S)-phenylsulfonyl-amino-b-alanine, 2-S-(n-butylsulfonylamino)-3[4-piperdin-4-yl)butyloxypheyl]propionic acid hydrochloride, (R)-methyl-3-[[[3-[4-(aminoiminomethyl)phenyl]-4,5-dihydro-5-isoxazolyl]acetyl]amino]-N-(butoxycarbonyl)-L-alanine monoacetate, xemlofiban, orbofiban, eptifibatide and mixtures thereof.

18. The method of claim 17 wherein the dermatan sulfate has more than about 75% repeating L-iduronic acid→4,6-di-O-sulfated N-acetyl-D-galactosamine disaccharide units.

19. The method of claim 12 wherein the administration step comprises injecting the heparin cofactor II agonist and the platelet GPIIb/IIIa receptor antagonist into the mammal.

20. The method of claim 19 wherein the mammal is a human.

* * * * *

UNITED STATES PATENT AND TRADEMARK OFFICE
CERTIFICATE OF CORRECTION

PATENT NO. : 6,518,244 B2
DATED : February 11, 2003
INVENTOR(S) : Alan D. Cardin et al.

It is certified that error appears in the above-identified patent and that said Letters Patent is hereby corrected as shown below:

Column 1,
Line 10, after the word "March 9, 2000" -- and copending U.S. Provisional Patent Application Serial No. 60/256,516, filed December 20, 2000 -- should be inserted.

Column 7,
Line 46, the word -- hydrabamine -- should be inserted and the word "hydrabarnine" should be deleted.

Column 9,
Line 66, after the word "propionyl)", a -- ; -- should be inserted.

Column 10,
Line 5, after the word "(piperidin-4-yl)", the word -- butyloxyphenyl]propionic -- should be inserted and the word "buteloxyphenyl]propionic" should be deleted.
Line 54, after "5,795,868", please insert -- 5,795,867 -- and "5,795.867" should be deleted.

Column 14,
Line 27, after the word "cholesterol,", the word -- stearylamine -- should be inserted and the word "stearylarnine" should be deleted.

Column 16,
Line 30, after the word "[4-piperdin-4-yl)", the word -- butyloxyphenyl]propionic -- should be inserted and the word "butyloxypheyl]propionic" should be deleted.

UNITED STATES PATENT AND TRADEMARK OFFICE
CERTIFICATE OF CORRECTION

PATENT NO.    : 6,518,244 B2
DATED         : February 11, 2003
INVENTOR(S)   : Alan D. Cardin et al.

It is certified that error appears in the above-identified patent and that said Letters Patent is hereby corrected as shown below:

<u>Column 17</u>,
Line 8, delete "8-etrahydro-4-oxo-5-[2-(piperidin-4-yl)ethyl]-4H-pyrazolo-" and replace with -- 8- tetrahydro-4-oxo-5-[2-(piperidin-4-yl)ethyl]-4H-pyrazolo -- (added extra space after "8-").
Lines 12 and 13, after the word "3[4-piperdin-4-yl)", the word -- butyloxyphenyl] propioni -- should be inserted and the word "butyloxypheyl]propionic" should be deleted.

Signed and Sealed this

Twenty-fifth Day of November, 2003

JAMES E. ROGAN
*Director of the United States Patent and Trademark Office*

UNITED STATES PATENT AND TRADEMARK OFFICE
CERTIFICATE OF CORRECTION

| | | |
|---|---|---|
| PATENT NO. | : 6,518,244 B2 | Page 1 of 1 |
| APPLICATION NO. | : 09/802775 | |
| DATED | : February 11, 2003 | |
| INVENTOR(S) | : Alan D. Cardin and Cornelius L. Van Gorp | |

It is certified that error appears in the above-identified patent and that said Letters Patent is hereby corrected as shown below:

On the Title Page

Item (73) Assignee should read: Smithfield Bioscience, Inc., Cincinnati, Ohio 45241

Signed and Sealed this
Sixth Day of July, 2021

Drew Hirshfeld
*Performing the Functions and Duties of the*
*Under Secretary of Commerce for Intellectual Property and*
*Director of the United States Patent and Trademark Office*